(12) United States Patent
Ito et al.

(10) Patent No.: US 9,788,732 B2
(45) Date of Patent: Oct. 17, 2017

(54) OPTICAL MEASURING DEVICE AND FIBER BUNDLE ASSOCIATION METHOD

(71) Applicant: OLYMPUS CORPORATION, Tokyo (JP)

(72) Inventors: Ryosuke Ito, Hino (JP); Kenji Kamimura, Hachioji (JP); Kazuhiro Gono, Sagamihara (JP); Takeshi Suga, Hino (JP); Masahiro Katakura, Chofu (JP); Yoshimine Kobayashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 493 days.

(21) Appl. No.: 14/477,507

(22) Filed: Sep. 4, 2014

(65) Prior Publication Data
US 2014/0371602 A1    Dec. 18, 2014

Related U.S. Application Data

(63) Continuation of application No. PCT/JP2013/056186, filed on Mar. 6, 2013.
(Continued)

(51) Int. Cl.
*A61B 1/00* (2006.01)
*A61B 5/00* (2006.01)

(52) U.S. Cl.
CPC .......... *A61B 5/0084* (2013.01); *A61B 5/0075* (2013.01)

(58) Field of Classification Search
CPC .................................. G01J 3/02; A61B 3/005
See application file for complete search history.

(56) References Cited

U.S. PATENT DOCUMENTS 6,524,237 B1   2/2003   McGowan
7,652,772 B2   1/2010   Backman et al.
(Continued)

FOREIGN PATENT DOCUMENTS

CA   2653040 A1   11/2007
JP   A-2009-537014   10/2009
(Continued)

OTHER PUBLICATIONS

Jun. 14, 2016 Office Action issued in Japanese Patent Application No. 2014-503522.
(Continued)

*Primary Examiner* — Michael D Abreu
(74) *Attorney, Agent, or Firm* — Oliff PLC

(57) ABSTRACT

An optical measuring device includes: a light source unit; a measurement probe including a fiber bundle, an illumination fiber that illuminates a living tissue with a illumination light, and a plurality of light-receiving fibers that receives return light of the illumination light reflected and/or scattered at the living tissue; a detection unit that receives the return light of the illumination light detected by the plurality of respective light-receiving fibers, and performs photoelectric conversion to detect respective signal intensities; and an association unit that associates the respective signal intensities detected by the detection unit with distances from the illumination fiber to the respective light-receiving fibers on an end face of a distal end portion of the measurement probe, when light having an intensity gradient around the illumination fiber is projected to the end face of the distal end portion of the measurement probe.

18 Claims, 15 Drawing Sheets

Related U.S. Application Data

(60) Provisional application No. 61/607,822, filed on Mar. 7, 2012.

(56) References Cited

U.S. PATENT DOCUMENTS

| | | | |
|---|---|---|---|
| 2004/0037554 A1 | 2/2004 | Ferguson et al. | |
| 2007/0129615 A1 | 6/2007 | Backman et al. | |
| 2008/0037024 A1 | 2/2008 | Backman et al. | |
| 2009/0009759 A1* | 1/2009 | Backman ........... | A61B 1/00096 356/303 |
| 2009/0294645 A1 | 12/2009 | Gorenstein et al. | |
| 2010/0182405 A1 | 7/2010 | Monteiro | |
| 2014/0025342 A1 | 1/2014 | Gorenstein et al. | |

FOREIGN PATENT DOCUMENTS

| | | |
|---|---|---|
| JP | A-2009-537285 | 10/2009 |
| JP | A-2009-539067 | 11/2009 |
| WO | 2007/133684 A2 | 11/2007 |

OTHER PUBLICATIONS

Jun. 29, 2015 Extended Search Report issued in European Patent Application No. 13757862.1.

May 7, 2013 International Search Report issued in International Application No. PCT/JP2013/056186.

Kim, Young L. et al., "Low-coherence Enhance Backscattering: Review of Principles and Applications for Colon Cancer Screening," *Journal of Biomedical Optics*, vol. 11 No. 4, pp. 041125 1-10, Aug./Jul. 2006.

Turzhitsky, Vladimir et al., "Characterization of Light Transport in Scattering Media at Subdiffusion Length Scales with Low-Coherence Enhanced Backscattering," *IEEE Journal of Selected Topics in Quantum Electronics*, vol. 16, No. 3, pp. 619-626, May/Jun. 2010.

Roy, Hemant K. et al., "Association between Rectal Optical Signatures and Colonic Neoplasia: Potential Applications for Screening," *Cancer Research*, vol. 69, No. 10, pp. 4476-4483, May 15, 2009.

* cited by examiner

| ORDER | FIBER ADDRESS |
|---|---|
| 1 | (c, 5) |
| 2 | (d, 3) |
| 3 | (b, 5) |
| 4 | (g, 1) |
| 5 | (a, 1) |
| 6 | (e, 4) |
| 7 | ... |

|   | 1 | 2 | 3 | 4 | 5 | 6 | 7 |
|---|---|---|---|---|---|---|---|
| a |   |   |   |   |   |   |   |
| b |   | 22 | 10 | 11 | 12 |   |   |
| c |   | 21 | 6 | 2 | 7 | 13 |   |
| d |   | 20 | 5 | 1 | 3 | 14 |   |
| e |   | 19 | 9 | 4 | 8 | 15 |   |
| f |   |   | 18 | 17 | 16 |   |   |
| g |   |   |   |   |   |   |   |

OPTICAL MEASURING DEVICE AND FIBER BUNDLE ASSOCIATION METHOD

CROSS-REFERENCE TO RELATED APPLICATIONS

This application is a continuation of PCT international application No. PCT/JP2013/056186 filed on Mar. 6, 2013 which designates the United States, incorporated herein by reference, and which claims the benefit of priority from U.S. provisional application No. 61/607,822, filed on Mar. 7, 2012, incorporated herein by reference.

BACKGROUND OF THE INVENTION

1. Field of the Invention

The present invention relates to an optical measuring device configured to illuminate a living tissue with measurement light, and based on a measurement value of the measurement light reflected and/or scattered from the living tissue, estimate characterization of the living tissue, and also relates to a fiber bundle association method.

2. Description of the Related Art

Conventionally, it is known that backscattering return light from a relatively weak scattering medium such as a living tissue is observed as interference enhanced light corresponding to the spatial coherence of the illumination light (see Young L. Kim, et. al, "Low-coherence enhanced backscattering; review of principles and applications for colon cancer screening", Journal of Biomedical Optics, 11(4), 041125, 2006). A spectrum information measurement technology using this phenomenon is called low-coherence enhanced backscattering spectroscopy (LEBS), and characteristics of an interference pattern with respect to a scattering mean free path (reciprocal of a scattering coefficient) in a scattering medium are well studied (see V, Turzhitsky, et. al, "Characterization of Light transport in Scattering Media at Subdiffusion Length Scales with Low-Coherence Enhanced Backscattering", IEEE journal of selected topics in quantum electronics, Vol. 16, No. 3, 619 (2010)). The scattering mean free path is correlated with the internal structural change of the scattering medium, which is used for detection of a minute tissue structural change which can be seen in early-stage cancer. For example, it is known that screening of colon cancer can be performed by using an interference pattern of scattering return light (see Hemant K. Roy, et. al, "Association between Rectal Optical Signatures and Colonic Neoplasia: Potential Applications for Screening", Cancer Research, 69(10), 4476 (2009)).

Regarding the LEBS described above, a technique of applying the LEBS to non-invasive measurement in the body, through a measurement probe inserted in an endoscope, is known (see US 2009/0009759 A). In this technique, in order to obtain an interference pattern, a living tissue is illuminated with illumination light from the distal end of an illumination fiber of a measurement probe, and the intensity distribution of scattered light at a plurality of positions, which are correspond to scattering angles, are measured using a plurality of light-receiving fibers to thereby detect characterization of the living tissue.

Further, a technique of detecting characterization of a living tissue using a measurement probe, configured of a fiber bundle formed by bundling a plurality of optical fibers, is known (see U.S. Pat. No. 7,652,772 B). In this technique, characterization of a living tissue is detected by associating arrangements of the respective optical fibers on the end faces of the distal end portion and the proximal end portion of the fiber bundle.

SUMMARY OF THE INVENTION

An optical measuring device according to one aspect of the present invention includes: a light source unit that emits light for measuring a living tissue; a measurement probe including a fiber bundle configured by bundling a plurality of optical fibers at random, the measurement probe including an illumination fiber that propagates light from the light source unit to a distal end as illumination light and illuminates the living tissue with the illumination light, and a plurality of light-receiving fibers that receives return light of the illumination light illumined by the illumination fiber and reflected and/or scattered at the living tissue; a detection unit that receives the return light of the illumination light detected by the plurality of respective light-receiving fibers, and performs photoelectric conversion to detect respective signal intensities; and an association unit that associates the respective signal intensities detected by the detection unit with distances from the illumination fiber to the respective light-receiving fibers on an end face of a distal end portion of the measurement probe, when light having an intensity gradient around the illumination fiber is projected to the end face of the distal end portion of the measurement probe.

A fiber bundle association method according to another aspect of the present invention is executed by an optical measuring device, the optical measuring device including: a light source unit that emits light for measuring a living tissue; a measurement probe including a fiber bundle configured by bundling a plurality of optical fibers at random, the measurement probe including an illumination fiber that propagates light from the light source unit to a distal end as illumination light and illuminates the living tissue with the illumination light, and a plurality of light-receiving fibers that receives return light of the illumination light illumined by the illumination fiber and reflected and/or scattered at the living tissue; and a detection unit that receives the return light of the illumination light detected by the plurality of respective light-receiving fibers and performs photoelectric conversion to detect respective signal intensities. The method includes an association step for associating the respective signal intensities detected by the detection unit with distances from the illumination fiber to the respective light-receiving fibers on an end face of a distal end portion of the measurement probe, when light having an intensity gradient around the illumination fiber is projected to the end face of the distal end portion of the measurement probe.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 10 illustrate a table in which the numbers of the light-receiving fibers are listed in descending order of the detected intensity of the measurement probe of the optical measuring device according to the embodiment of the present invention;

FIG. 11 is a diagram illustrating the order of intensities of the respective light-receiving fibers in the distal end portion of the measurement probe of the optical measuring device according to the embodiment of the present invention;

DETAILED DESCRIPTION OF THE PREFERRED EMBODIMENTS

Hereinafter, as a preferred embodiment of an optical measuring device and a fiber bundle association method according to the present invention, an optical measuring device using LEGS will be described, as an example, in detail with reference to the drawings. Further, the present invention is not limited to this embodiment. Further, same parts are described by denoting same reference signs in the description of the drawings. Further, the drawings are schematic views, and it should be noted that the relation between the thickness and the width of each member and ratios between the respective members, for example, differ from real. Further, among the drawings, portions different in dimensions and ratios thereof are included.

Figure 1:
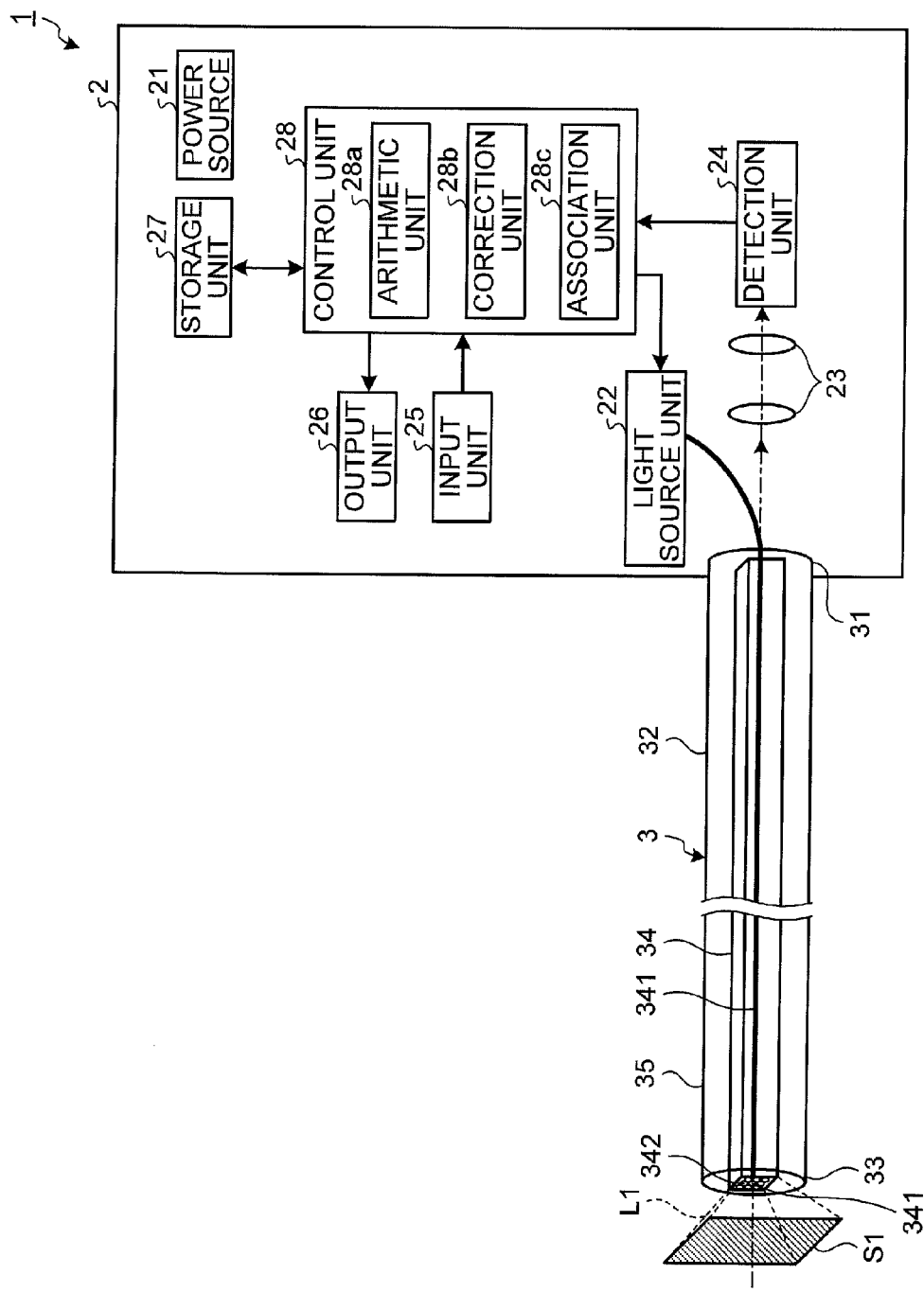
FIG. 1 is a schematic configuration diagram schematically illustrating an optical measuring device according to an embodiment of the present invention.

FIG. 1 is a schematic configuration diagram schematically illustrating an optical measuring device according to an embodiment of the present invention. An optical measuring device 1 illustrated in FIG. 1 includes a main body unit 2 which performs optical measurement on a measurement target S1 such as a living tissue which is a scatter to thereby measure the optical property of the measurement target S1, and a measurement probe 3 which is connected with the main body unit 2 detachably, and is inserted in a subject via a treatment tool channel of an endoscope.

First, the main body unit 2 will be described. The main body unit 2 includes a power source 21, a light source unit 22, an optical system 23, a detection unit 24, an input unit 25, an output unit 26, a recording unit 27, and a control unit 28. The power source 21 supplies electric power to the respective constituent units of the main body unit 2.

The light source unit 22 emits, to the measurement probe 3, light having at least one spectral component which illuminates a measurement target, as illumination light. The light source unit 22 is configured by using a light source such as a light emitting diode (LED), a xenon lamp, a tungsten lamp, a halogen lamp, or a laser, an optical system including a plurality of lens such as a condenser lens and a collimating lens, for example, and a light source driver and the like. The light source unit 22 emits illumination light to the measurement probe 3 under control of the control unit 28. For example, the light source unit 22 switches between lighting and extinction of the illumination light under control of the control unit 28. The light source unit 22 condenses the light emitted from a light source (not illustrated) on the illumination fiber of the measurement probe 3, described below, by means of an optical system (not illustrated). Thereby, luminous flux coupling efficiency between the light source and the measurement probe 3 increases, and the amount of illumination light increases, whereby it is possible to improve the measurement quality of the measurement target S1.

The optical system 23 relays the intensity of the plurality of fibers at the proximal end 31 to the optical sensor inside the detection unit 24. The optical system 23 is configured by using a plurality of lens such as a condenser lens and a collimating lens.

The detection unit 24 detects return light of illumination light which is emitted from the distal end of the measurement probe 3 via the optical system 23 and is reflected and/or scattered at the measurement target S1, and outputs the detection result (signal intensity) to the control unit 28. The detection unit 24 is configured by using a two-dimensional optical sensor or the like such as a charge coupled device (CCD) or a complementary metal oxide semiconductor (CMOS). When the number of the light-receiving fibers of the measurement probe 3, described below, is small, the detection unit 24 may be configured by using a plurality of photosensitivity detectors such as a photo diode PD), avalanche photo diode (APD), a Photomultiplier tube (PMT).

The input unit 25 receives an input of an instruction signal instructing activation of the main body unit 2 or an instruction signal instructing another type of operation, and outputs the input to the control unit 28. The input unit 25 is configured by using input devices such as a push-type switch, a touch panel, a keyboard, a mouse.

The output unit 26 outputs information relating to various types of processing in the optical measuring device 1, and measurement results of the measurement target. The output unit 26 is configured by using a display such as a liquid crystal display, an organic Electro Luminescence (EL) display, a speaker, and the like.

The recording unit 27 records various programs for operating the optical measuring device 1, and various types of data and various types of parameters used for optical measurement processing. The recording unit 27 temporarily records information during processing of the optical measuring device 1. Further, the recording unit 27 records measurement results of the measurement target. The recording unit 27 is configured by using a volatile memory, non-volatile memory, or the like. The recording unit 27 may be configured by using a memory card or the like loaded from the outside of the main body unit 2.

The control unit 28 controls processing operation of the respective units of the main body unit 2. The control unit 28 performs transfer of instruction information and data, or the like, to the respective units of the main body unit 2, for example, to thereby collectively control operation of the main body unit 2. The control unit 28 is configured by using a central processing unit (CPU) or the like. The control unit 28 also includes an arithmetic unit 28a, a correction unit 28b, and an association unit 28c.

The arithmetic unit 28a performs a plurality of units of arithmetic processing based on the detection results detected by the detection unit 24 to thereby calculate characteristic values of the optical property and characterization of the measurement target. The types of the characteristic values are set according to the instruction signal received by the input unit 25 or various types of programs recorded on the recording unit 27.

The correction unit 28b is configured to, when light in which the intensity is spatially uniform is emitted from a distal end portion 33 of the measurement probe 3 and is received on a plurality of light-receiving fibers, smooth the respective signal intensities of the light-receiving fibers detected by the detection unit 24 to thereby correct the sensitivity of each of the detection unit 24 and the measurement probe 3.

The association unit 28c is configured to, when light having an intensity gradient around a illumination fiber 341 is projected to an end face 33a of the distal end portion 33 of the measurement probe 3, associate the respective signal intensities in the light-receiving fibers of the measurement probe 3, described below, detected by the detection unit 24, and the distances of the respective light-receiving fibers from the illumination fiber 341 on the end face 33a of the distal end portion 33 of the measurement probe 3, and records the signal intensities and the distances in the recording unit 27. Specifically, the association unit 28c is configured to, when light having a spatial profile of symmetric intensity distribution around the illumination fiber 341 is projected to the end face 33a of the distal end portion 33 of the measurement probe 3, associate the respective signal intensities detected by the detection unit, the respective signal intensities in the light-receiving fibers of the measurement probe 3, described below, detected by the detection unit 24, and the distances from the illumination fibers 341 on the end face 33a of the distal end portion 33 of the measurement probe 3, and record the signal intensities and the distances on the recording unit 27. For example, the association unit 28c sequentially associates the signal intensities detected by the detection unit 24 in descending order of the signal intensity, with the light-receiving fibers of the plurality of the light-receiving fibers of the measurement probe in order of the light-receiving fibers arranged at closer positions in distance from the illumination fiber on the end face of the distal end portion of the measurement probe 3, and records them on the recording unit 27.

Next, the measurement probe 3 will be described. The measurement probe 3 illustrated in FIG. 1 includes a proximal end portion 31 detachably connected with the main body unit 2, a flexible portion 32 having flexibility, the distal end portion 33 which illuminates the measurement target S1 with illumination light supplied from the light source unit 22 and receives return light of the illumination light reflected and/or scattered at the measurement target S1, a fiber bundle 34 which propagates the illumination light received from the proximal end portion 31 to the distal end portion 33, and also propagates return light of the illumination light reflected and/or scattered at the measurement target S1, received by the distal end portion 33, to the detection unit 24, and a coated portion 35 which covers the fiber bundle 34 for light shielding and damage prevention of the fiber bundle 34.

The fiber bundle 34 is configured by using a plurality of optical fibers. Specifically, the fiber bundle 34 is configured by using a light guide or a random fiber in which optical fibers are bundled at random, or an image fiber in which optical fibers are bundled regularly. More preferably, the fiber bundle 34 is configured by using a light guide or a random fiber. Here, a light guide is one in which the arrangement positions (spatial arrangement) of the respective optical fibers are different between an end face 31a of the proximal end portion 31 of the fiber bundle 34 and on an end face 33a of the distal end portion 33 of the fiber bundle 34. The fiber bundle 34 also includes the illumination fiber 341 which illuminates the measurement target S1 with illumination light supplied from the light source unit 22, and a plurality of light-receiving fibers 342 which receives return light of the illumination light reflected and/or scattered at the measurement target S1.

Figure 2:
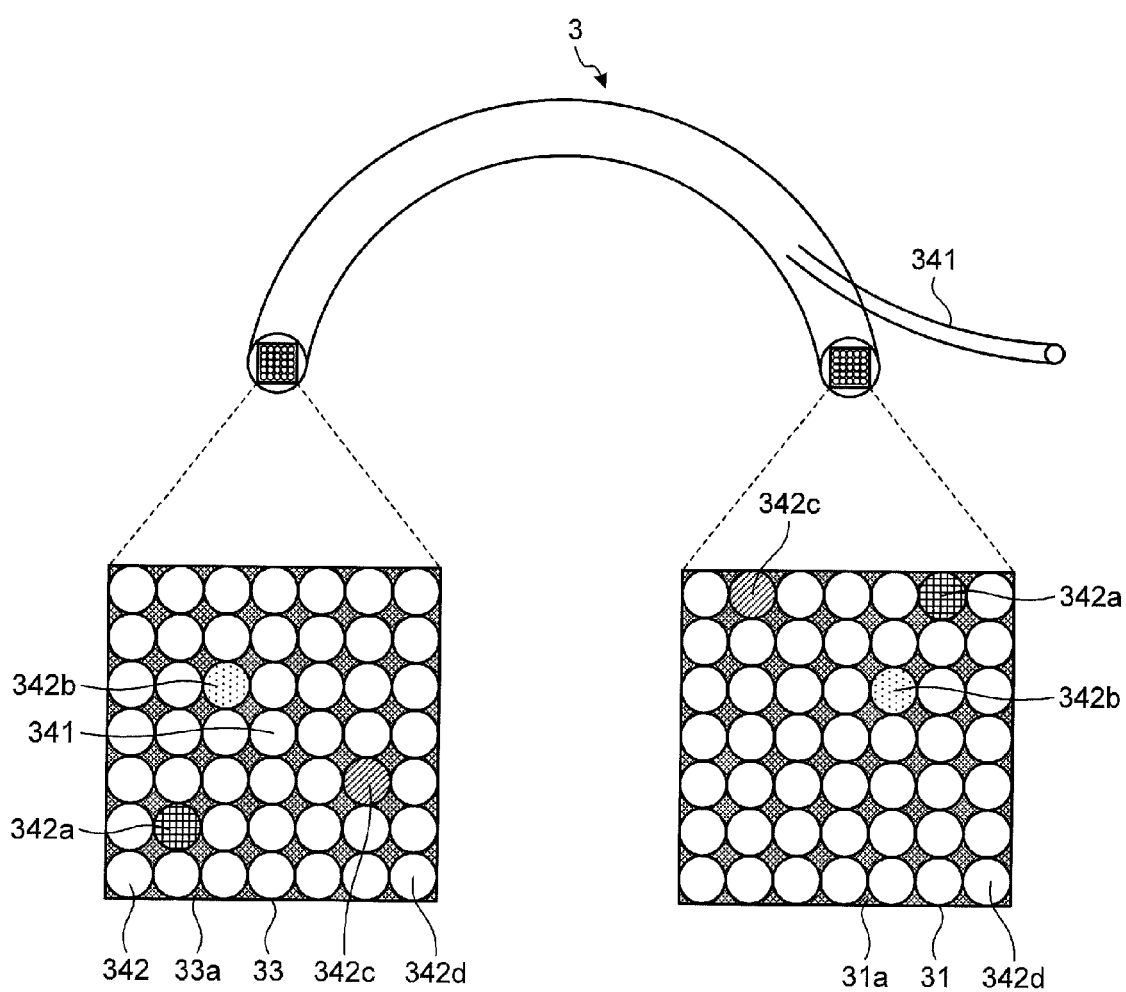
FIG. 2 is a schematic diagram in which a main part of a fiber bundle of a measurement probe of the optical measuring device, according to the embodiment of the present invention, is enlarged.

Here, the configuration of the fiber bundle 34 of the measurement probe 3 will be described in detail. FIG. 2 is a schematic diagram in which the main part of the fiber bundle 34 of the measurement probe 3 is enlarged.

As illustrated in FIG. 2, the fiber bundle 34 includes the illumination fiber 341 which propagates the illumination light supplied from the light source unit 22 and illuminates the measurement target S1 from the distal end portion 33 of the measurement probe 3, and the light-receiving fibers 342 on which return light from the measurement target S1 is received at different positions. For example, the fiber bundle 34 is configured by bundling a first light-receiving fiber 342a (first light-receiving channel), a second light-receiving fiber 342b (second light-receiving channel), and a third light-receiving fiber 342c (third light-receiving channel), on which return light from the measurement target S1 is received at different positions, and other optical fibers 342d, at random.

As described above, the fiber bundle 34 is configured such that the respective arrangement positions (positional coordinates) of the illumination fiber 341, the first light-receiving fiber 342a, the second light-receiving fiber 342b, the third light-receiving fiber 342c, and the other optical fibers 342d are different between the end face 33a of the distal end portion 33 and the end face 31a of the proximal end portion 31. FIG. 2 illustrates an example in which the hatched one in the proximal end portion 31 and the hatched one in the distal end portion 33 satisfy a correspondence relationship. Further, in FIG. 2, the positions of the first light-receiving fiber 342a, the second light-receiving fiber 342b, the third light-receiving fiber 342c, and the other optical fibers 342d are set from among the optical fibers configuring the fiber bundle 34 according to the association processing described below.

The illumination fiber 341 propagates the illumination light supplied from the light source unit 22, and illuminates the measurement target S1 with the illumination light. The number of illumination fibers 341 can be changed appropriately according to the test item and the type of measurement target, for example, bloodstream, a region of stomach, pancreatic.

The first light-receiving fiber 342a, the second light-receiving fiber 342b, and the third light-receiving fiber 342c propagate return light from the measurement target S1 received from the end face 33a of the distal end portion 33, and emit the return light to the detection unit 24 via the optical system 23. The number of light-receiving fibers can be changed appropriately according to the test item and the type of measurement target, for example, bloodstream or a region.

In the optical measuring device 1 configured in this way, the measurement probe 3 is inserted into the subject via a treatment tool channel provided to the endoscope, and the illumination fiber 341 illuminates the measurement target S1 with illumination light, and the first light-receiving fiber 342a, the second light-receiving fiber 342b, and the third light-receiving fiber 342c respectively receive return light from the measurement target S1 and propagate the return light to the detection unit 24 of the main body unit 2. Then, the arithmetic unit 28a calculates the optical property of the measurement target S1, based on the detection result of the detection unit 24.

Figure 3:
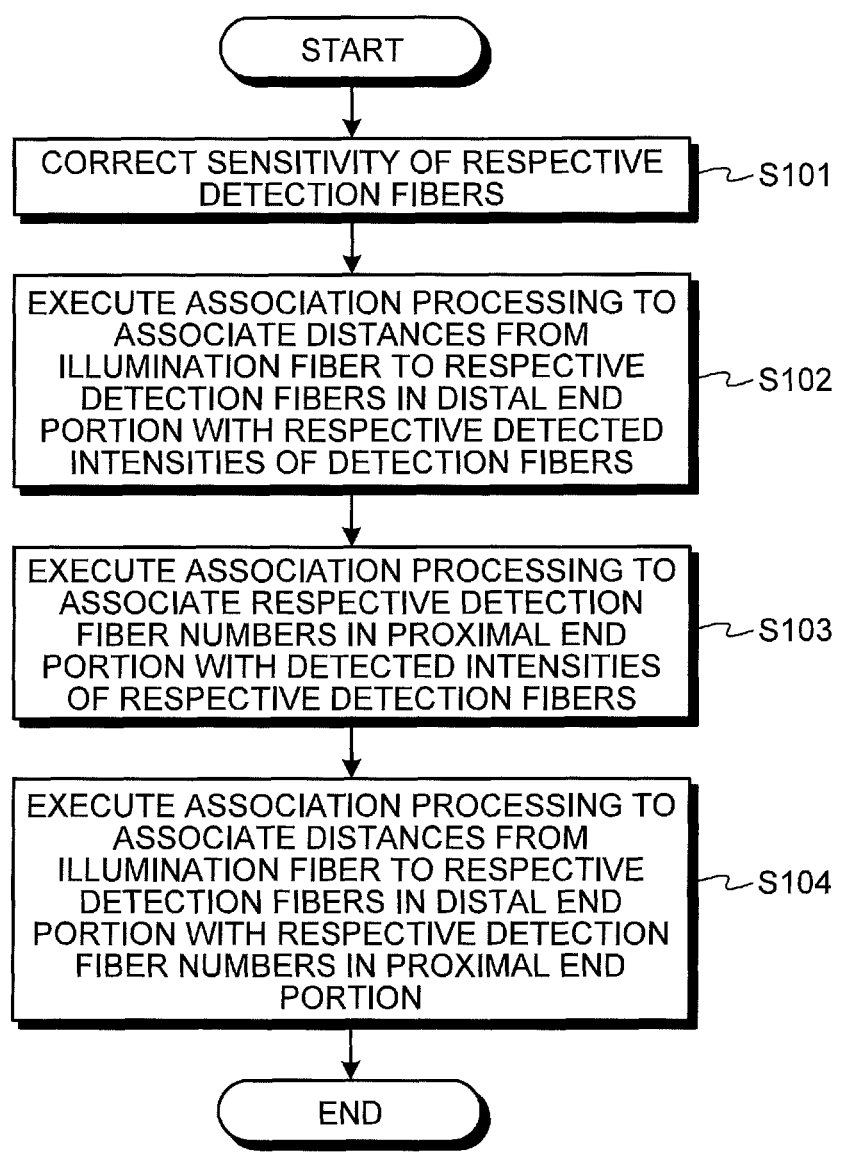
FIG. 3 is a flowchart illustrating the outline of fiber bundle association processing executed by the optical measuring device according to the embodiment of the present invention.

Next, association processing to associate distances from the illumination fiber 341 to the respective light-receiving fibers 342 in the distal end portion 33, with signal intensities detected by the detection unit 24 via the respective light-receiving fibers 342, executed by the optical measuring device 1, will be described. FIG. 3 is a flowchart illustrating the outline of the association processing of the fiber bundle 34 executed by the optical measuring device 1.

As illustrated in FIG. 3, the correction unit 28b first corrects the detection sensitivities of the respective light-receiving fibers 342 of the measurement probe 3 (step S101). Specifically, when light having a specially uniform intensity is received on the respective light-receiving fibers 342 from the distal end portion 33 of the measurement probe 3, the correction unit 28b executes calibration processing to correct the sensitivity of the detection unit 24 such that the detection sensitivities of the respective light-receiving fibers 342 become uniform, based on the respective detection intensities corresponding to the respective light-receiving fibers 342 detected by the detection unit 24 (correction step). In this case, it is preferable that the incidence NA of the light-receiving fiber 342 of the measurement target S1 and the incidence NA of the light-receiving fiber 342 of the light having a spatially uniform intensity when the sensitivity is corrected are substantially equal. Thereby, the correction unit 28b can perform sensitivity correction more stably. Consequently, the detection unit 24 can detect a uniform value corresponding to the respective light-receiving fibers 342 with respect to the light having a spatially uniform intensity. The detection unit 24 detects the detection intensity (signal intensity) by receiving light for each of the pixels corresponding to the respective light-receiving fibers 342 and performing photoelectric conversion, or detect an average value of the detection intensities with respect to a plurality of pixels corresponding to the respective light-receiving fibers 342 forming a set.

Then, the association unit 28c executes association processing to associate the distances from the illumination fiber 341 to the respective light-receiving fibers 342 in the distal end portion 33, with the detected intensities of the respective light-receiving fibers 342 (step S102). Specifically, the optical measuring device 1 projects, from the end face 33a of the distal end portion 33 of the measurement probe 3, light having an intensity gradient around the illumination fiber 341, for example, light having a spatial profile of symmetrical intensity distribution around the illumination fiber 341 (projection step).

Figure 4:
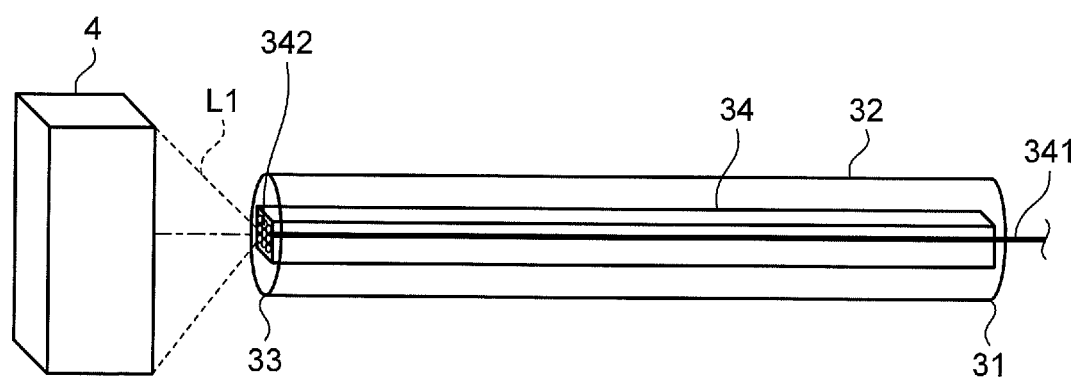
FIG. 4 is a schematic diagram illustrating the case of generating, in the distal end portion of the measurement probe, a spatial profile in which an intensity gradient varies symmetrically around an illumination fiber on an end face of the distal end portion of the measurement probe of the optical measuring device according to the embodiment of the present invention.
Figure 5:
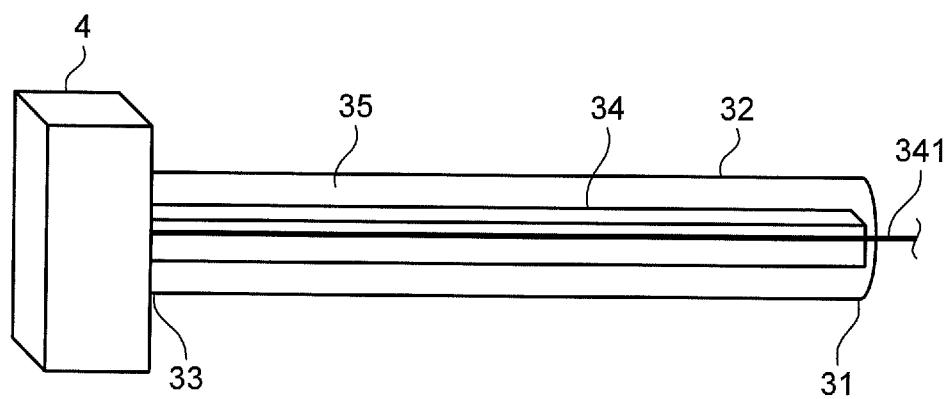
FIG. 5 is a schematic diagram illustrating the case of generating, in the distal end portion of the measurement probe, a spatial profile in which an intensity gradient varies symmetrically around the illumination fiber on an end face of the distal end portion of the measurement probe of the optical measuring device according to the embodiment of the present invention.

FIG. 4 is a schematic diagram illustrating the case of generating a spatial profile in which the intensity gradient varies symmetrically around the illumination fiber 341, on the end face 33a of the distal end portion 33 of the measurement probe 3. As illustrated in FIG. 4, the optical measuring device 1 illuminates a light-scattering member 4 having uniform scattering property, disposed at a position away from the distal end portion 33 of the measurement probe 3 by a predetermined distance, with illumination light from the illumination fiber 341 to thereby project light having a spatial profile onto (make light incident on) the distal end portion 33 of each of the light-receiving fibers 342. Here, the light-scattering member 4 is formed of a material which uniformly scatters light having a wavelength of a measurement target efficiently. Specifically, the light-scattering member 4 may be formed of solution or resin in which scattering particles are uniformly distributed in a transparent medium such as milk. Alternatively, as the light-scattering member 4, a white standard reflector may be used, for example. Further, as illustrated in FIG. 5, the optical measuring device 1 may emit illumination light from the illumination fiber 341 in a state where the light-scattering member 4 is closely attached to the distal end portion 33 of the measurement probe 3.

Figure 6:
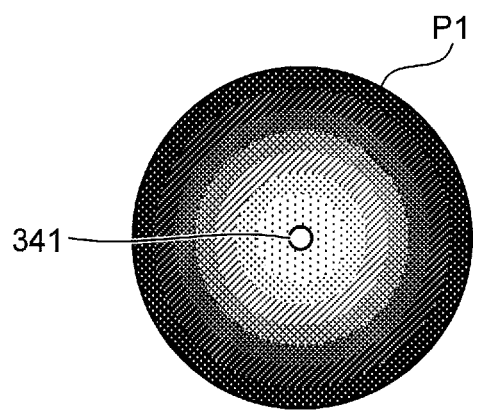
FIG. 6 is a view schematically illustrating a spatial profile when a light scattering member is illuminated with illumination light.

FIG. 6 is a schematic view illustrating a spatial profile when the light-scattering member 4 is illuminated with illumination light. The light intensity received by each of the light-receiving fibers 342 in the distal end portion 33 varies according to the distance from the illumination fiber 341. Specifically, as illustrated in FIG. 6, a spatial profile P1 has distribution such that the light intensity is higher at a closer position around the illumination fiber 341, and the light intensity becomes lower sequentially as the distance from the illumination fiber 341 increases toward the outer edge (concentric pattern).

Here, a state where the optical measuring device 1 projects light having a special profile in which the light intensity varies around the illumination fiber 341, to the distal end portion 33 of the measurement probe 3.

Figure 7:
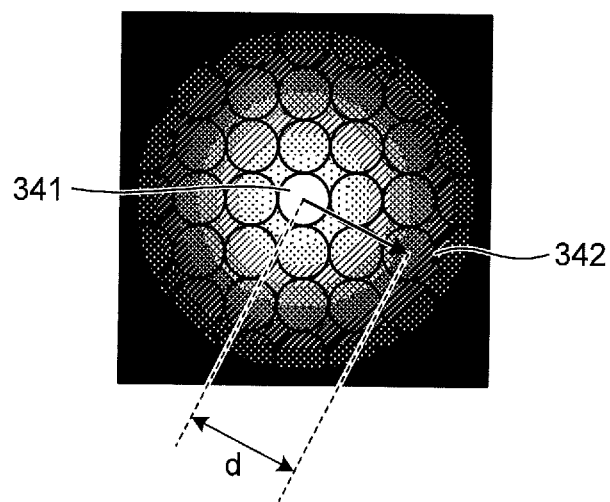
FIG. 7 is a view illustrating a state where light having a spatial profile, in which the light intensity varies around the illumination fiber, is projected to the distal end portion of the measurement probe of the optical measuring device according to the embodiment of the present invention.
Figure 8:
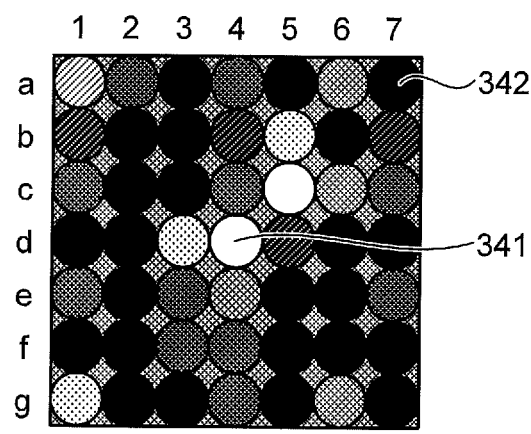
FIG. 8 is a view illustrating distribution of light intensities of respective light-receiving fibers in the proximal end portion when light having a spatial profile, in which the light intensity varies around the illumination fiber, is projected to the distal end portion of the measurement probe of the optical measuring device according to the embodiment of the present invention.

FIG. 7 is a view illustrating a state where light having the spatial profile P1, in which the light intensity varies around the illumination fiber 341, is projected to the distal end portion 33 of the measurement probe 3. FIG. 8 is a view illustrating distribution of the light intensities of the respective light-receiving fibers 342 in the proximal end portion 31 when light having the spatial profile P1, in which the light intensity varies around the illumination fiber 341, is projected to the distal end portion 33 of the measurement probe 3.

As illustrate in FIG. 7, the spatial profile P1 is configured such that the light intensity detected by the light-receiving fiber 342, away from the illumination fiber 341 by a distance d, is lowered, for example. In this case, as illustrated in FIG. 8, as the fiber bundle 34 is configured such that the positions of the respective light-receiving fibers 342 in the proximal end portion 31 and the positions of the respective light-receiving fibers 342 in the distal end portion 33 are different, the light intensities are distributed non-uniformly in the proximal end portion 31.

Returning to FIG. 3, the description after step S103 will be continued. At step S103, the association unit 28c executes association processing to associate the numbers (addresses) of the respective light-receiving fibers 342 in the proximal end portion 31, with the detected intensities of the respective light-receiving fibers 342.

Figure 9:
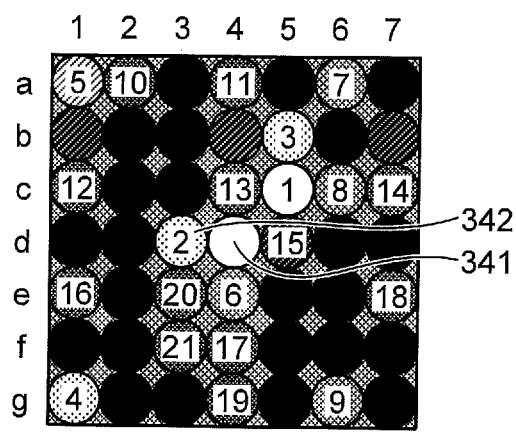
FIG. 9 is a view illustrating the numbers of the respective light-receiving fibers in the proximal end portion of the measurement probe of the optical measuring device, and the order of detected intensities of the respective light-receiving fibers, according to the embodiment of the present invention.

FIG. 9 is a view illustrating the numbers of the respective light-receiving fibers 342 in the proximal end portion 31, and the order of the detected intensities of the respective light-receiving fibers 342. FIG. 10 illustrates a table in which the numbers of the light-receiving fibers 342 are listed in descending order of the detected intensity. The number in each of the light-receiving fibers 342 in FIG. 9 illustrates the order of the detected intensity of the light-receiving fiber 342 in the proximal end portion 31. Specifically, the detected intensity is smaller as the number is larger.

As illustrated in FIG. 9 and FIG. 10, based on the detection results detected by the detection unit 24, the association unit 28c generates a table T1 in which the numbers (addresses) of the respective light-receiving fibers 342 in the proximal end portion 31 are associated with the detected intensities of the respective light-receiving fibers 342, and records the table T1 on the recording unit 27. For example, as illustrated in FIG. 10, the association unit 28c generates the table T1 in which the number "c" vertically and the number "5" horizontally of the light-receiving fiber 342 in the proximal end portion 31 are associated with the light-receiving fiber 342 in which the order of the detected intensity is one.

Then, the association unit 28c executes association processing to associate the distances from the illumination fiber 341 to the respective light-receiving fibers 342 in the distal end portion 33 of the measurement probe 3, with the numbers of the respective light-receiving fibers 342 in the proximal end portion 31 of the measurement probe 3 (step S104).

FIG. 11 is a view illustrating the intensity order of the respective light-receiving fibers 342 in the distal end portion 33. As illustrated in FIG. 11, the association unit 28c sets the order of the light-receiving fibers 342 in the distal end portion 33 corresponding to the distance from the illumination fiber 341, where the order of the illumination fiber 341 is one. Specifically, as illustrated in FIG. 11, the association unit 28c sets a higher order to the light-receiving fiber 342 having a closer distance from the illumination fiber 341. For example, as illustrated in FIG. 11, the association unit 28c sets the number "4, c" of the light-receiving fiber 342 to "2", "5, d" to "3", "4, e" to "4", and "3, d" to "5", respectively. Thereby, based on the detected intensities (table T1 in FIG. 10) and the light intensities (table T2 in FIG. 11) corresponding to the distances from the illumination fiber 341 to the respective light-receiving fibers 342 in the distal end portion 33, the association unit 28c can associate the positions of the respective light-receiving fibers 342 on the end face 33a of the distal end portion 33 and on the end face 31a of the proximal end portion 31 of the fiber bundle 34.

Figure 12:
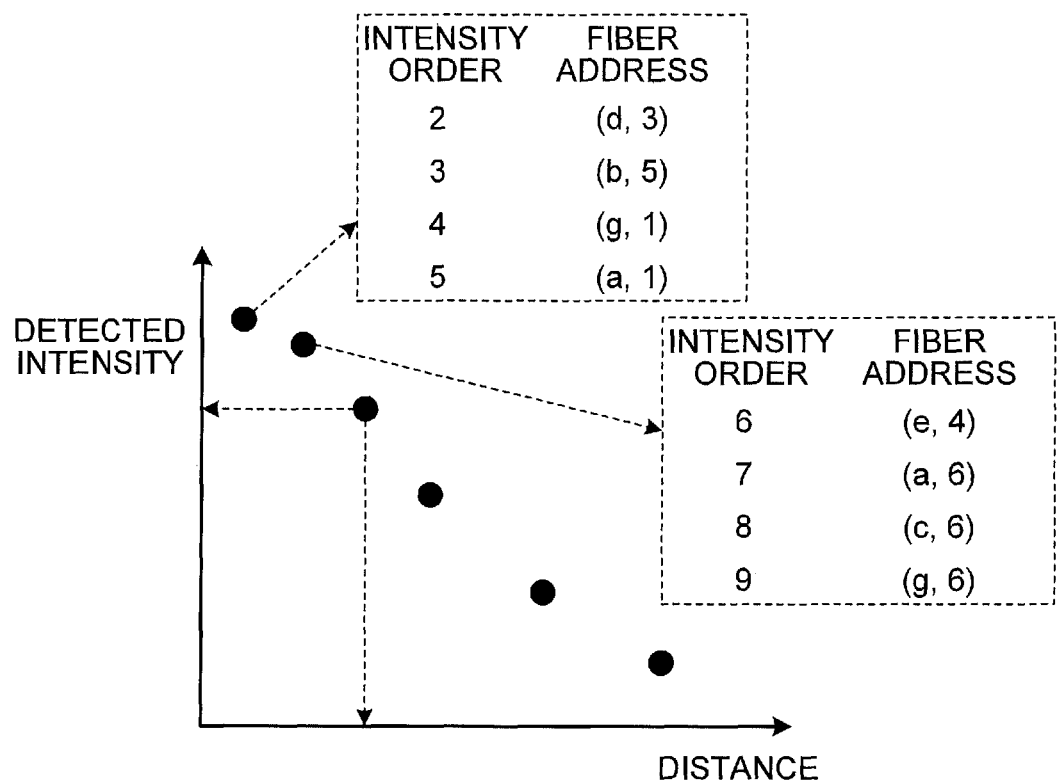
FIG. 12 is a diagram illustrating a relationship between the distances from the illumination fiber of the measurement probe of the optical measuring device of the optical device to the respective light-receiving fibers, and detected intensities detected by the respective light-receiving fibers, according to the embodiment of the present invention.

FIG. 12 is a diagram illustrating a relationship between the distances from the illumination fiber 341 to the respective light-receiving fibers 342 and the detected intensities detected by the respective light-receiving fibers 342. As illustrated in FIG. 12, regarding the distances from the illumination fiber 341 to the respective light-receiving fibers 342 in the distal end portion 33 of the measurement probe 3, as the distances of the respective light-receiving fibers 342 in the proximal end portion 31 are discrete, the detected intensities of the respective light-receiving fibers 342 in the proximal end portion 31 are also discrete. As such, based on the table T1 in FIG. 10 and the table T2 in FIG. 11, the association unit 28c performs grouping by the distances from the illumination fiber 341 to the respective light-receiving fibers 342 on the end face 33a of the distal end portion 33 of the measurement probe 3, and performs collective association such that respective signal intensities corresponding to the grouping are put into one signal intensity. Specifically, the association unit 28c puts the light-receiving fibers 342, which are the nearest to the illumination fiber 341 on the end face 33a in the distal end portion 33 of the measurement probe 3, into one group, and associates this group with position numbers (fiber addresses) of the light-receiving fibers 342 in descending order of the detected intensities in the proximal end portion 31. For example, with reference to the table T2 illustrated in FIG. 11, the association unit 28c associates four light-receiving fibers 342 (c, 4), (d, 5), (e, 4), and (d, 3) having the same distance from the illumination fiber 341 on the end face 33a of the distal end portion 33 of the measurement probe 3, with the intensity orders 2(d, 3), 3(b, 5), 4(g, 1), and 5(a, 1) on the end face 31a of the proximal end portion 31 of the measurement probe 3. Thereby, the association unit 28c can virtually associate the arrangements of the respective light-receiving fibers 342 on the end face 31a of the proximal end portion 31 and on the end face 33a of the distal end portion 33 of the measurement probe 3.

According to the embodiment described above, as the association unit 28c projects the spatial profile P1 in which the intensity varies around the illumination fiber 341, and performs association of the distance from the illumination fiber 341 to the respective light-receiving fibers 342 based on the respective signal intensities detected by the detection unit 24, it is possible to perform analysis of LEGS signals or intensity attenuation distribution on the surface of the scattering medium by using the random fiber bundle 34 in which the positional coordinates of the respective optical fibers are not set.

Further, according to the embodiment of the present invention, as the fiber bundle 34 in which the light-receiving fibers are arranged at random in the distal end portion 33 and in the proximal end portion 31 is used, it is possible to reduce the manufacturing costs.

Further, according to the embodiment, by projecting light having the spatial profile P1 in which the intensity varies axisymmetrically around the illumination fiber 341, the detected intensities detected by the respective light-receiving fibers 342 on the end face 33a of the distal end portion 33 vary according to the distance from the illumination fiber 341. Thereby, based on the detected intensities of the respective light-receiving fibers 342 on the end face 31a of the proximal end portions 31, it is possible to associate the distances of the light-receiving fibers 342 from the illumination fiber 341 on the end face 33a of the distal end portion 33.

Further, according to the embodiment of the present invention, as a method of obtaining the spatial profile P1 in which the intensity varies axisymmetrically around the illumination fiber 341, a spatial profile for the association work described above can be obtained by measuring the light-scattering member 4 by means of the method same as the measurement of the measurement target S1. As such, even if actual measurement is performed, association processing can be performed easily.

Further, according to the embodiment of the present invention, as a method of obtaining the spatial profile P1 in which the intensity varies axisymmetrically around the illumination fiber 341, it is only necessary to use the light-scattering member 4. As such, generation of light having the spatial profile P1 can be performed easily.

Further, according to the embodiment, it is possible to perform analysis based on the distance from the illumination fiber 341, and to perform more detailed analysis. For example, comparison with a scattering simulation can be performed.

Further, according to the embodiment of the present invention, as the association unit 28c corrects the sensitivity of the respective light-receiving fiber 342 by smoothing the signal intensities of the light-receiving fibers 342 detected by the detection unit 24 when uniform light is received on the distal end portion 33 of the measurement probe 3, it is possible to perform more accurate measurement. Results of sensitivity correction performed by the association unit 28c may be recorded on the recording unit 27 in advance.

Further, according to the embodiment, the association unit 28c may perform association of the fiber bundle 34 as described above each time a new measurement probe 3 is connected with the main body unit 2.

Further, according to the embodiment, when the measurement probe 3 is fixed to the main body unit 2, or the same measurement probe 3 is connected with the main body unit 2, it is possible to record the results of the above-described association processing performed by the association unit 28c on the recording unit 27 and reuse the results.

OTHER EMBODIMENTS

Figure 13:
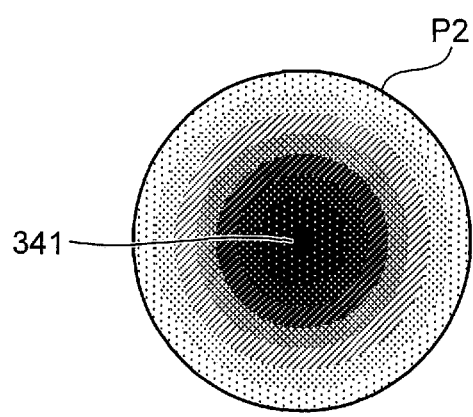
FIG. 13 is a view schematically illustrating another spatial profile when a light-scattering member is illuminated with illumination light.

In the present invention, the spatial profile projected to the distal end portion 33 of the measurement probe 3 can be changed. FIG. 13 is a view schematically illustrating another spatial profile when the light-scattering member 4 is illuminated with illumination light.

Figure 14:
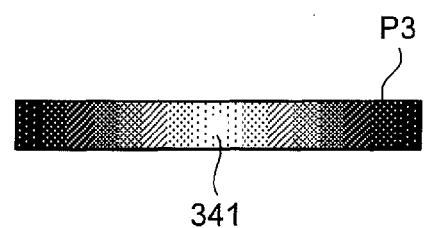
FIG. 14 is a view schematically illustrating another spatial profile.

A spatial profile P2 illustrated in FIG. 13 may have distribution in which the light intensity is lower at a position closer to the illumination fiber 341 which is the center, and the light intensity gradually increases at a position farther from the illumination fiber 341 toward the outer edge. Further, it is also possible to project light only to one example of the fiber bundle 34, like a spatial profile P3 illustrated in FIG. 14.

Figure 15:
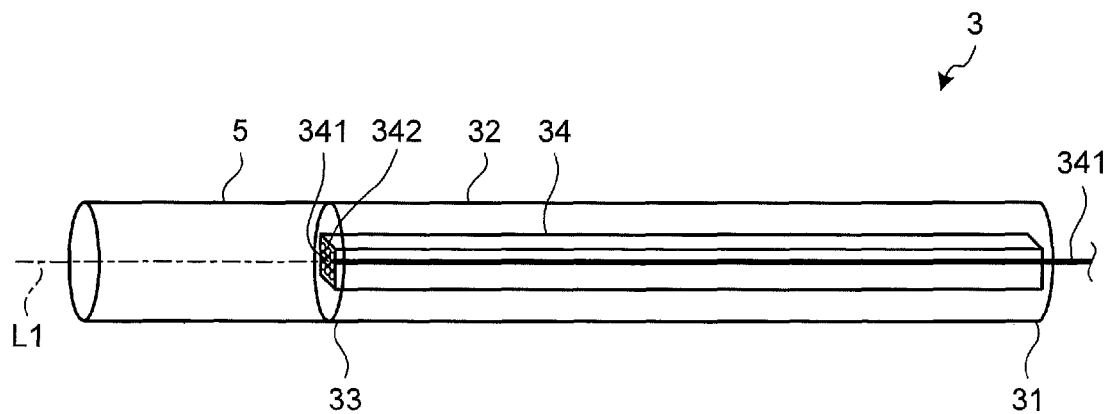
FIG. 15 is a schematic configuration diagram in the case where an optical member is provided to the distal end portion of the measurement probe of the optical measuring device according to the embodiment of the present invention.

Further, in the present invention, it is also possible to provide an optical member 5, which causes distances between the measurement target S1 and the illumination fiber 341 and the light-receiving fiber 342 to be constant, to the distal end portion 33 of the measurement probe 3. FIG. 15 is a schematic diagram illustrating a state where the optical member 5 is provided to the distal end portion 33 of the measurement probe 3 of the optical measuring device 1.

As illustrated in FIG. 15, the optical member 5 relays the illumination light emitted from the illumination fiber 341 and illuminates the measurement target S1 with the illumination light, and also relays the return light of the illumination light from the measurement target S1 to the light-receiving fiber 342. The optical member 5 is configured by using a material such as glass material, plastic having a prescribed refractive index.

Thereby, the optical measuring device 1 can measure the measurement target S1 without being affected by the irregularities on the surface of the measurement target S1. The distal end portion of the optical member 5 may be cut off at an angle with respect to the longitudinal direction so as to form an inclined surface. Further, the optical member 5 may be a gas such as air, or a liquid such as water, provided that it can relay light having a measurement wavelength. In that case, it is only necessary to use a hollow member made of metal or resin.

Further, the optical member 5 may be attachable/detachable with respect to the distal end portion 33 of the measurement probe 3. Thereby, it is possible to perform optical measurement in which the distance between the measurement target S1 and the distal end of the measurement probe 3 is set by the measurement target S1. Further, the optical member 5 may be configured to be attachable and detachable by providing a male screw and a female screw to the linking portions (not illustrated) respectively. Of course, the optical member 5 may be configured to be attachable and detachable by forming a groove on one side and forming a claw on the other side.

Figure 16:
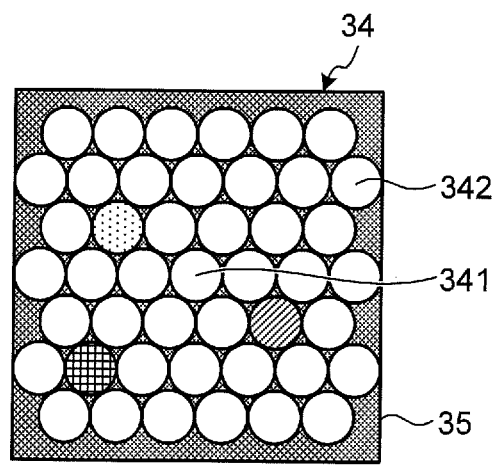
FIG. 16 is a view illustrating an example of the distal end portion in which the illumination fiber and the light-receiving fibers of the fiber bundle, in the measurement probe of the optical measuring device, are arranged in a hexagonal close shape, according to the embodiment of the present invention.
Figure 17:
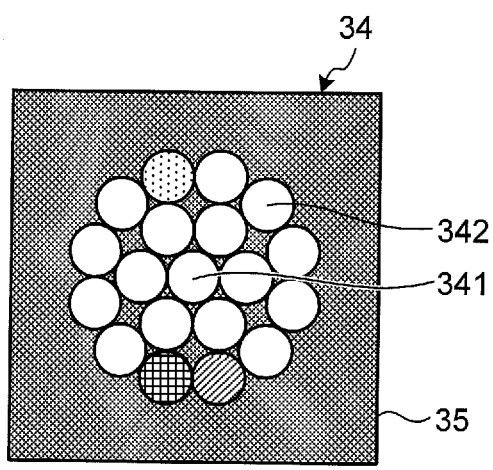
FIG. 17 is a view illustrating another example of the distal end portion in which the illumination fiber and the light-receiving fibers of the fiber bundle, in the measurement probe of the optical measuring device, are arranged concentrically, according to the embodiment of the present invention.
Figure 18:
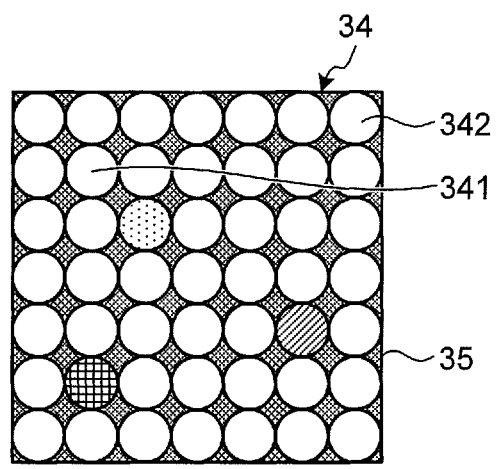
FIG. 18 is a view illustrating an example of the distal end portion in which the illumination fiber and the light-receiving fibers of the fiber bundle, in the measurement probe of the optical measuring device, are arranged in a lattice shape, and the illumination fiber is arranged at a position shifted from the center of the fiber bundle, according to the embodiment of the present invention.
Figure 19:
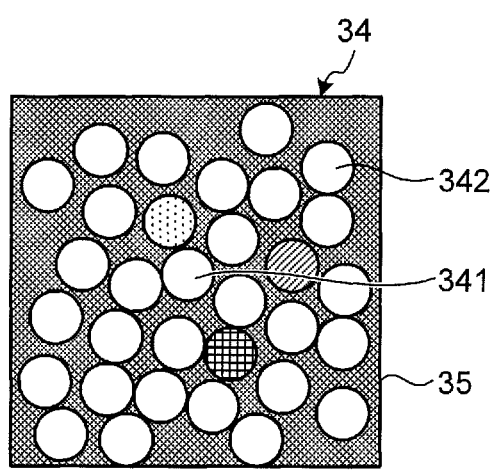
FIG. 19 is a view illustrating an example of the distal end portion in which the illumination fiber and the light-receiving fibers of the fiber bundle, in the measurement probe of the optical measuring device, are arranged at random, according to the embodiment of the present invention.

Further, in the present invention, the fiber bundle 34 having a different arrangement may be used. FIG. 16 is a view illustrating an example of the distal end portion 33 in which the illumination fiber 341 and the light-receiving fibers 342 are arranged in a hexagonal close shape. FIG. 17 illustrates another example of the distal end portion 33 in which the illumination fiber 341 and the light-receiving fibers 342 are arranged concentrically. FIG. 18 is a view illustrating an example of the distal end portion 33 in which the illumination fiber 341 and the light-receiving fibers 342 are arranged in a lattice shape, and the illumination fiber 341 is arranged at a position shifted from the center of the fiber bundle 34. FIG. 19 is a view illustrating an example of the distal end portion 33 in which the illumination fiber 341 and the light-receiving fibers 342 are arranged at random.

The association unit 28c can perform positioning of the light-receiving fibers 342 in the distal end portion 33 and the light-receiving fibers 342 in the proximal end portion 31 even in the case of using the fiber bundle 34 arranged as illustrated in FIG. 16 to FIG. 19, by performing the association processing as described above.

Figure 20:
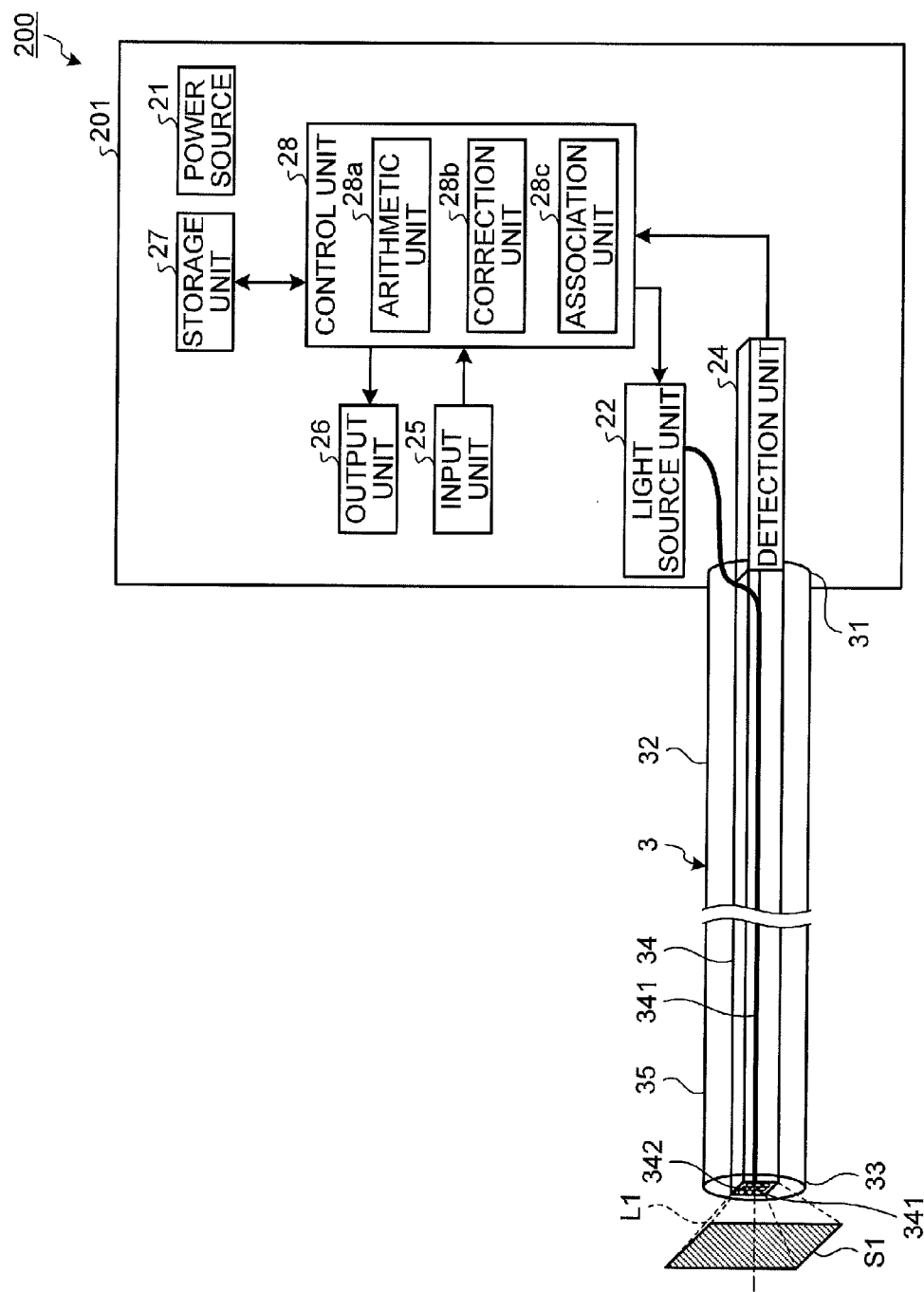
FIG. 20 is a schematic configuration diagram schematically illustrating an optical measuring device according to a first variation of the embodiment of the present invention.

Further, in the present invention, a method of connecting the light source unit 22 and the illumination fiber 341 can be changed. FIG. 20 is a schematic configuration diagram schematically illustrating an optical measuring device according to a first variation of the embodiment of the present invention.

An optical measuring device 200 illustrated in FIG. 20 is configured such that the illumination fiber 341 extending individually from the middle of the fiber bundle 34 is connected with the light source unit 22 of a main body unit 201. In this case, the detection unit 24 may be connected with the proximal end portion 31 of the measurement probe 3.

Figure 21:
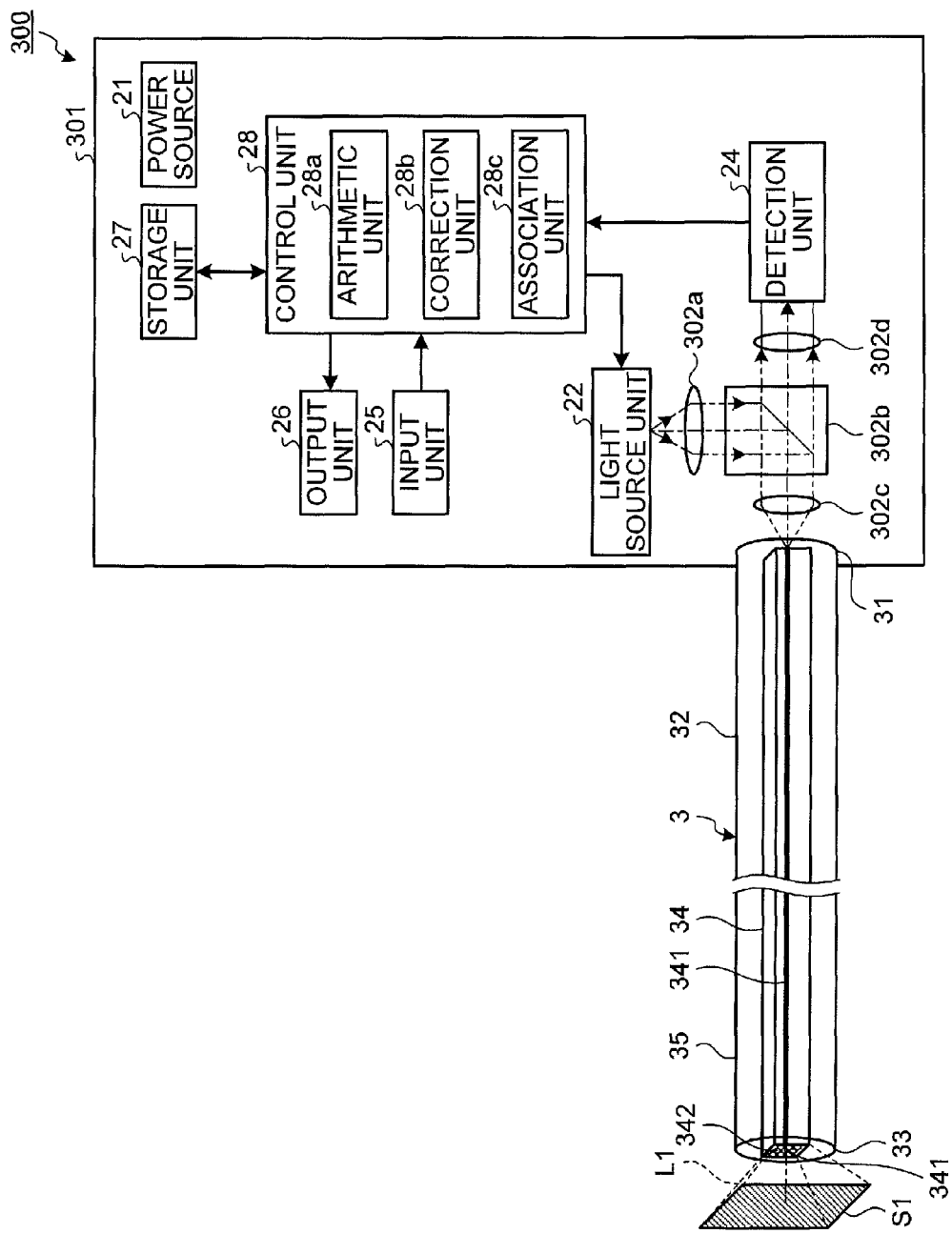
FIG. 21 is a schematic configuration diagram schematically illustrating an optical measuring device according to a second variation of the embodiment of the present invention.

Further, in the present invention, a method of connecting the light source unit 22 and the illumination fiber 341 can be further changed. FIG. 21 is a schematic configuration diagram schematically illustrating an optical measuring device according to a second variation of the embodiment of the present invention.

An optical measuring device 300 illustrated in FIG. 21 includes an optical system 302 which reflects illumination light, with which the light source unit 22 illuminates a main body unit 301, toward the illumination fiber 341 of the measurement probe 3, and transmits the return light of the illumination light from the measurement target S1 emitted from the respective light-receiving fibers 342 of the measurement probe 3, to the detection unit 24. The optical system 302 includes a condenser lens 302a which condenses illumination light emitted from the light source unit 22, a light dividing element 302b which reflects the illumination light emitted from the condenser lens 302a toward the illumination fiber 341 of the measurement probe 3, and transmits the return light of the illumination light from the measurement target emitted from the measurement probe 3, a condenser lens 302c which condenses the return light of the illumination light from the measurement target S1 emitted from the measurement probe 3, and condenses the illumination light reflected from the light dividing element 302b on the illumination fiber 341, and a collimating lens 302d which propagates the return light of the illumination light passing through the light dividing element 302b.

Figure 22:
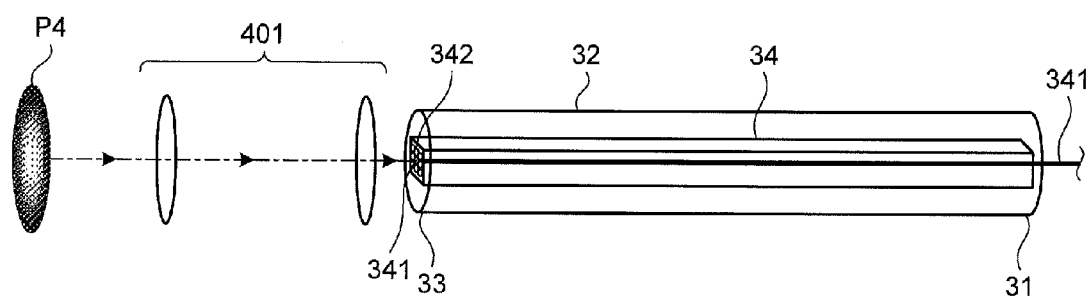
FIG. 22 is another schematic diagram illustrating the case where a spatial profile, in which the intensity varies in an axisymmetric manner around the illumination fiber of the measurement probe of the optical measuring device, is generated in the distal end portion of the measurement probe, according to the embodiment of the present invention.

Further, in the present invention, a spatial profile in which the intensity varies in an axisymmetric manner around the illumination fiber 341 may be projected in another way from the distal end portion 33 of the measurement probe 3. FIG. 22 is another schematic diagram illustrating the case where a spatial profile, in which the intensity varies in an axisymmetric manner around the illumination fiber 341, is generated in the distal end portion 33 of the measurement probe 3.

As illustrated in FIG. 22, projection is performed in such a manner that the center of at least one type of primary image P4, in which the intensity varies concentrically via a relay optical system 401, and the center of the illumination fiber 341 in the distal end portion 33 of the measurement probe 3 are aligned. Thereby, based on the pattern of the primary image P4 and the magnification of the relay optical system 401, the association unit 28c can associate the intensity distribution of the light-receiving fibers 342 in the distal end portion 33 and the distance of the illumination fiber 341. Further, in the method of projecting a primary image, a spatial profile can be controlled easily, and the method is easily applicable in the case of obtaining a well-known spatial profile.

Figure 23:
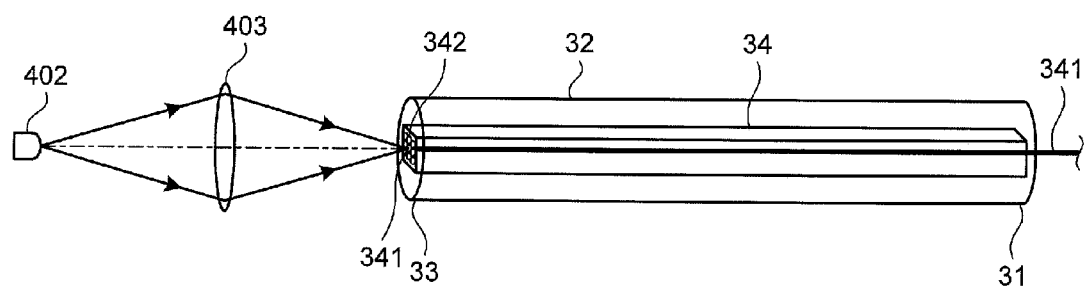
FIG. 23 is another schematic diagram illustrating the case where light having a spatial profile, in which the light intensity varies around the illumination fiber of the measurement probe of the optical measuring device, is generated in the distal end portion of the measurement probe, according to the embodiment of the present invention.

Further, in the present invention, light having a spatial profile in which the intensity varies in an axisymmetric manner around the illumination fiber 341 may be projected in another way from the distal end portion 33 of the measurement probe 3. FIG. 23 is another schematic diagram illustrating the case of generating light having a spatial profile in which the intensity varies around the illumination fiber 341, in the distal end portion 33 of the measurement probe 3.

Figure 24:
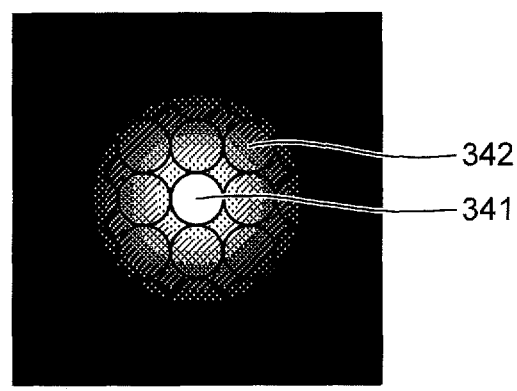
FIG. 24 is a view schematically illustrating a spatial profile which is projected in the state illustrated in FIG. 23.

As illustrated in FIG. 23, wavelength long light having one wavelength is received on the illumination fiber 341 of the distal end portion 33 of the measurement probe 3 via a condenser lens 403, by an external light source 402 configured of a laser or the like. Thereby, the clad thickness of the illumination fiber 341 leaks the wavelength long light, and the spatial profile in which light of a measurement target wavelength is contained is projected to the distal end portion 33. Specifically, the spatial profile illustrated in FIG. 24 is projected to the distal end portion 33 of the measurement probe 3. As the external light source 402, emitted light from an illumination fiber having a core diameter which is the same as or smaller than the core diameter of the illumination fiber 341 of the measurement probe 3 may be used. In that case, light obtained from any light source such as a LED, a xenon lamp may be used.

Further, in the present invention, the wavelength range of the illumination light should be optimized for acquiring information of a living tissue, and can be set arbitrarily depending on those to which the wavelength range is applied. When spectral information is useful, a wider range covering the wavelength range can be set, or a plurality of bands can be set discretely, or the band may be limited to some extent if unnecessary.

Further, in the present invention, the detection unit 24 may measure a detection value of each wavelength by detecting the spectral component and the intensity distribution of the light which is received from the light-receiving fiber 342 of the measurement probe 3, propagates inside the measurement target S1, and returns. In that case, the detection unit 24 is only necessary to use a spectral device such as a diffraction grating for spectrum. The spectral device such as a diffraction grating is desirably disposed in the parallel optical path of the relay optical system.

According to the embodiments of the present invention, the association unit associates respective signal intensities of light-receiving fibers detected by the detection unit and distances from the illumination fiber to the light-receiving fibers on the end face of the distal end portion of the measurement probe, when light having an intensity gradient around the illumination fiber is projected to the end face of the distal end portion of the measurement probe. Accordingly, the present invention exhibits an advantageous effect that positions of the respective fibers on the end faces of the distal end portion and the proximal end portion of a fiber bundle can be associated with each other, with a simple configuration.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical measuring device comprising:
   a light source unit that emits light for measuring a living tissue;
   a measurement probe including a fiber bundle configured by bundling a plurality of optical fibers at random, the fiber bundle including an illumination fiber that propagates light from the light source unit to a distal end as illumination light and illuminates the living tissue with the illumination light, and a plurality of light-receiving fibers that receives return light of the illumination light illumined by the illumination fiber and reflected and/or scattered at the living tissue, wherein each of the plurality of optical fibers is arranged such that a position in an arrangement of the optical fibers on an end face of a proximal end portion and a position arrangement of the optical fibers on an end face of a distal end portion are different from each other;
   a detection unit that receives the return light of the illumination light detected by the plurality of respective light-receiving fibers, and performs photoelectric conversion to detect respective signal intensities; and
   an association unit that associates the respective signal intensities detected by the detection unit with distances from the illumination fiber to the respective light-receiving fibers on the end face of the distal end portion of the measurement probe, when light having an intensity gradient around the illumination fiber is projected to two or more light receiving fibers whose distances from the illumination fiber are different from each other on the end face of the distal end portion of the measurement probe in order to estimate characterization of the living tissue.

2. The optical measuring device according to claim 1, wherein the association unit associates the respective signal intensities detected by the detection unit with the distances from the illumination fiber to the respective light-receiving fibers on the end face of the distal end portion of the measurement probe, when light having a spatial profile of symmetric intensity distribution around the illumination fiber is projected to the end face of the distal end portion of the measurement probe.

3. The optical measuring device according to claim 2, wherein the fiber bundle is a light guide.

4. The optical measuring device according to claim 1, wherein the association unit sequentially associates the respective signal intensities detected by the detection unit in descending order of the signal intensity, with the light-receiving fibers of the plurality of the light-receiving fibers in order of closer distance from the illumination fiber on the end face of the distal end portion of the measurement probe.

5. The optical measuring device according to claim 4, wherein the fiber bundle is a light guide.

6. The optical measuring device according to claim 1, wherein the association unit performs grouping by the respective distances from the illumination fiber to the plurality of light-receiving fibers on the end face of the distal end portion of the measurement probe based on the respective signal intensities detected by the detection unit, and associates collectively the respective signal intensities corresponding to each of groups as one signal intensity.

7. The optical measuring device according to claim 6, wherein the fiber bundle is a light guide.

8. The optical measuring device according to claim 1, further comprising a correction unit that smooths the respective signal intensities detected by the detection unit when light having a spatially uniform intensity is received on end faces of the plurality of light-receiving fibers from the distal end portion of the measurement probe.

9. The optical measuring device according to claim 8, wherein the fiber bundle is a light guide.

10. The optical measuring device according to claim 1, wherein the fiber bundle is configured such that an arrangement of the optical fibers on an end face of a proximal end portion and an arrangement of the optical fibers on an end face of a distal end portion are different from each other.

11. The optical measuring device according to claim 10, wherein the fiber bundle is a light guide.

12. The optical measuring device according to claim 1, wherein the fiber bundle is a light guide.

13. The optical measuring device according to claim 1, further comprising an optical member provided to the distal end portion of the measurement probe, the optical member keeping distances between distal ends of the illumination fiber and the plurality of light-receiving fibers and the living tissue constant.

14. A fiber bundle association method executed by an optical measuring device, the optical measuring device including:
   a light source unit that emits light for measuring a living tissue;
   a measurement probe including a fiber bundle configured by bundling a plurality of optical fibers at random, the fiber bundle including an illumination fiber that propagates light from the light source unit to a distal end as illumination light and illuminates the living tissue with the illumination light, and a plurality of light-receiving fibers that receives return light of the illumination light illumined by the illumination fiber and reflected and/or scattered at the living tissue, wherein each of the plurality of optical fibers is arranged such that a position in an arrangement of the optical fibers on an end face of a proximal end portion and a position in the arrangement of the optical fibers on an end face of a distal end portion are different from each other; and
   a detection unit that receives the return light of the illumination light detected by the plurality of respective light-receiving fibers and performs photoelectric conversion to detect respective signal intensities, the method comprising:
   an association step for associating the respective signal intensities detected by the detection unit with distances from the illumination fiber to the respective light-receiving fibers on the end face of the distal end portion of the measurement probe, when light having an intensity gradient around the illumination fiber is projected to two or more light-receiving fibers whose distances from the illumination fiber ace different from each other on the end face of the distal end portion of the measurement probe in order to estimate characterization of the living tissue.

15. The fiber bundle association method according to claim 14, further comprising a projection step for projecting light having a spatial profile of symmetric intensity distribution around the illumination fiber, to the distal end portion of the measurement probe.

16. The fiber bundle association method according to claim 14, wherein the association step includes sequentially associating the respective signal intensities detected by the detection unit in descending order of the signal intensity, with the light-receiving fibers of the plurality of the light-receiving fibers in order of closer distance from the illumination fiber on the end face of the distal end portion of the measurement probe.

17. The fiber bundle association method according to claim 14, wherein in the association step performs grouping by the respective distances from the illumination fiber to the plurality of light-receiving fibers on the end face of the distal end portion of the measurement probe based on the respective signal intensities detected by the detection unit, and associates collectively the respective signal intensities corresponding to each of groups as one signal intensity.

18. The fiber bundle association method according to claim 14, further comprising a correction step for smoothing the respective signal intensities detected by the detection unit when light having a spatially uniform intensity is received on the plurality of light-receiving fibers from the distal end portion of the measurement probe.

* * * * *